US008932625B2

(12) United States Patent
Hashimoto et al.

(10) Patent No.: US 8,932,625 B2
(45) Date of Patent: Jan. 13, 2015

(54) EXTERNAL PATCH PREPARATION COMPRISING KETOPROFEN AND A SPECIFIC UV SCREENING AGENT

(75) Inventors: Yoshiaki Hashimoto, Tosu (JP); Yasunori Takada, Tosu (JP); Miyuki Shinmura, Tosu (JP); Shigeo Suzuki, Tosu (JP); Kiyomi Tsuruda, Tosu (JP); Koichi Ikesue, Tsukuba (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 622 days.

(21) Appl. No.: 10/584,739

(22) PCT Filed: Dec. 24, 2004

(86) PCT No.: PCT/JP2004/019327

§ 371 (c)(1), (2), (4) Date: Jun. 26, 2006

(87) PCT Pub. No.: WO2005/063215

PCT Pub. Date: Jul. 14, 2005

(65) Prior Publication Data

US 2007/0154531 A1 Jul. 5, 2007

(30) Foreign Application Priority Data

Dec. 26, 2003 (JP) ................................ 2003-434468

(51) Int. Cl.

| | |
|---|---|
| ***A61K 9/70*** | (2006.01) |
| ***A61K 31/192*** | (2006.01) |
| ***A61F 13/02*** | (2006.01) |
| ***A61K 9/00*** | (2006.01) |
| ***A61K 31/19*** | (2006.01) |

(52) U.S. Cl.

CPC ............. *A61K 9/7053* (2013.01); *A61K 9/0014* (2013.01); *A61K 31/19* (2013.01); *A61K 9/7038* (2013.01); *A61K 9/7076* (2013.01); *A61K 31/192* (2013.01)

USPC ........................... 424/449; 424/448; 514/569

(58) Field of Classification Search

None

See application file for complete search history.

(56) References Cited

U.S. PATENT DOCUMENTS

| | | | | |
|---|---|---|---|---|
| 4,489,057 | A * | 12/1984 | Welters et al. | 424/47 |
| 5,637,293 | A * | 6/1997 | Honda | 424/62 |
| 5,869,087 | A * | 2/1999 | Hirano et al. | 424/449 |
| 6,924,410 | B2 * | 8/2005 | Tsuruda et al. | 602/48 |
| 2003/0157138 | A1 * | 8/2003 | Eini et al. | 424/401 |
| 2004/0146548 | A1 * | 7/2004 | Takada et al. | 424/449 |
| 2005/0042269 | A1 * | 2/2005 | Tateishi et al. | 424/449 |
| 2005/0053646 | A1 * | 3/2005 | Yasukochi et al. | 424/449 |

FOREIGN PATENT DOCUMENTS

| | | | | |
|---|---|---|---|---|
| EP | 1234573 A1 | | 8/2002 | |
| EP | 1234573 B1 | | 7/2005 | |
| EP | 1661583 A1 | | 5/2006 | |
| EP | PCT/JP2004019327 | | 7/2012 | |
| FR | 2804024 A1 | | 7/2001 | |
| JP | 60-155111 | | 8/1985 | |
| JP | 03-076285 | | 4/1991 | |
| JP | 05-030118 | | 2/1993 | |
| JP | 09-012448 | | 1/1997 | |
| JP | 09-169658 | | 6/1997 | |
| JP | 10-265371 | | 10/1998 | |
| JP | 2000-136122 | | 5/2000 | |
| WO | WO 96/08245 | | 3/1996 | |
| WO | WO 01/68061 | | 9/2001 | |
| WO | WO 01/78690 | | 10/2001 | |
| WO | WO 02/34200 | | 5/2002 | |
| WO | WO 02/069942 | | 9/2002 | |
| WO | WO 03/037393 | * | 8/2003 | A61L 15/00 |

OTHER PUBLICATIONS

Mitsuo Toyama, "kan'atsusei Secchakuzai (Nenchakuzai)—Sono kino to shikumi-", 1991 pp. 185-186 with abridged English translation.

* cited by examiner

*Primary Examiner* — Kevin S Orwig

(74) *Attorney, Agent, or Firm* — Licata & Tyrrell P.C.

(57) ABSTRACT

An adhesive patch comprising a substrate and a pressure-sensitive adhesive base, wherein the pressure-sensitive adhesive base comprises a rubbery polymer having double bonds in the main chain and a nonsteroidal anti-inflammatory analgesic and contains a UVA screening agent and/or UVB screening agent as a stabilizer for the rubbery polymer. The adhesive patch is excellent in the stability of the pressure-sensitive adhesive base and in drug infiltration into the skin.

6 Claims, No Drawings

EXTERNAL PATCH PREPARATION COMPRISING KETOPROFEN AND A SPECIFIC UV SCREENING AGENT

This patent application is the National Stage of International Application No. PCT/JP2004/019327, filed Dec. 24, 2004, which claims the benefit of priority from Japanese Application No. 2003-434468, filed Dec. 26, 2003, each of which are herein incorporated by reference in their entirety.

TECHNICAL FIELD

The present invention relates to a patch comprising a rubber-system macromolecule having a double bond in a principal chain thereof, a nonsteroidal anti-inflammatory analgesic drug, and a UVA blocker and/or a UVB blocker as a stabilizer for a base.

BACKGROUND ART

Since patches are used by being affixed to the surface of the skin, they might be exposed to sunlight outdoors depending on the application site. Because of this, in a patch containing a compound that is susceptible to decomposition by UV rays from the sun, there are the problems that a drug within a base decomposes and cannot exhibit its proper efficacy, its photodecomposition products might induce side effects, etc.

As a way of avoiding such effects of UV rays, adding a UV blocker to the base or the support of a patch is usually tried. For example, an external preparation for percutaneous administration in which a UV absorber, etc. is added to a base in order to stabilize ketoprofen, which is unstable toward light (ref. Patent Publication 1), an anti-inflammatory external skin preparation to which titanium oxide is added in order to suppress photosensitivity to a nonsteroidal anti-inflammatory agent (ref. Patent Publication 2), an external skin preparation for preventing inflammation due to exposure to UV rays and the resulting skin reaction, etc. (Patent Publication 3), etc. are known. Furthermore, patches in which a UV absorber/blocker is added to or kneaded with a support of the patch (ref. Patent Publications 4 to 7), etc. have also been reported.

[Patent Publication 1]
JP, B, 5-8169
[Patent Publication 2]
JP, A, 9-169658
[Patent Publication 3]
JP, A, 2000-136122
[Patent Publication 4]
JP, A, 3-76285
[Patent Publication 5]
JP, UA, 5-30118
[Patent Publication 6]
JP, A, 10-265371
[Patent Publication 7]
WO 01/68061

DISCLOSURE OF INVENTION

Problems to be Solved by the Invention

While developing a patch containing a nonsteroidal anti-inflammatory analgesic drug, the present inventors have encountered the previously unknown problem that a patch containing a nonsteroidal anti-inflammatory analgesic drug and a rubber-system macromolecule having a double bond in a principal chain thereof in an adhesive base is degraded by exposure to UV rays, etc., thus causing stickiness and stringiness, etc., and have carried out further research in order to solve such a problem.

That is, it is an object of the present invention to solve the above-mentioned problem of a patch containing, in an adhesive base layer, a rubber-system macromolecule having a double bond in a principal chain thereof and a nonsteroidal anti-inflammatory analgesic drug.

Means for Solving the Problems

As a result of an intensive investigation by the present inventors in order to solve the above-mentioned problems, there has been discovered the completely new and previously unknown finding that not only is a rubber-system macromolecule having a double bond in a principal chain thereof readily degraded by exposure to UV rays and has poor light stability when the macromolecule is on its own, but when used in a combination with a nonsteroidal anti-inflammatory analgesic drug, the degradation of a rubber-system macromolecule having a double bond at least in a principal chain thereof, such as a styrene-isobutylene-styrene block copolymer, is also greatly accelerated by radicals formed as a result of decomposition of the drug due to the exposure to UV rays, etc.

As a result of further investigation by the present inventors, it has been found that by adding a UVA blocker and/or a UVB blocker, which suppress decomposition of a nonsteroidal anti-inflammatory analgesic drug effectively, it is possible to prevent the rubber-system macromolecule having a double bond from being degraded by radical formation, and the present invention has thus been accomplished.

That is, the present invention relates to a patch comprising a support and an adhesive base, the adhesive base containing a rubber-system macromolecule having a double bond at least in a principal chain thereof and a nonsteroidal anti-inflammatory analgesic drug, and further containing a UVA blocker and/or a UVB blocker as a stabilizer for the rubber-system macromolecule.

Furthermore, the present invention relates to the patch, wherein the rubber-system macromolecule having a double bond at least in a principal chain thereof is selected from the group consisting of a styrene-isoprene-styrene block copolymer, a styrene-butadiene-styrene block copolymer, a styrene-butadiene copolymer, polyisoprene, and polybutadiene.

Moreover, the present invention relates to the patch, wherein the nonsteroidal anti-inflammatory analgesic drug is selected from the group consisting of ketoprofen, tiaprofenic acid, suprofen, tolmetin, carprofen, benoxaprofen, piroxicam, meloxicam, benzydamine, naproxen, felbinac, diclofenac, ibuprofen, diflunisal, azapropazone, etodolac, valdecoxib, celecoxib, rofecoxib, and pharmaceutically acceptable salts thereof.

The present invention relates to the patch, wherein the UVA blocker is selected from the group consisting of a dibenzoylmethane derivative and a benzotriazole derivative.

Furthermore, the present invention relates to the patch, wherein the UVA blocker is selected from the group consisting of 4-tert-butyl-4'-methoxydibenzoylmethane, terephthalylidene-3,3'-dicamphor-10,10'-disulfonic acid, 2-(2H-benzotriazol-2-yl)-4-methyl-6-[2-methyl-3-[1,3,3,3-tetramethyl-1-[(trimethylsilyl)oxy]disiloxanyl]propyl]phenol, and 2-(2-hydroxy-5-methoxyphenyl)-benzotriazole.

Moreover, the present invention relates to the patch, wherein the UVB blocker is selected from the group consisting of a benzophenone derivative, a cinnamic acid derivative, a camphor derivative, an amino acid-based compound, and a benzoylpinacolone derivative.

The present invention relates to the patch, wherein a tackifier added to the adhesive base is one or more types selected from a rosin ester, a hydrogenated rosin ester, a maleic acid-modified rosin ester, a terpene resin, and a petroleum resin.

Furthermore, the present invention relates to the patch, wherein the tackifier added to the adhesive base is a combination of a hydrogenated rosin ester and a terpene resin.

Moreover, the present invention relates to the patch, wherein it contains 2 to 10 mass % of the UVA blocker and/or the UVB blocker in the adhesive base.

Furthermore, the present invention relates to the patch, wherein the amount of tackifier added is 10 to 20 mass %.

Moreover, the present invention relates to the patch, wherein it contains zinc oxide or titanium dioxide.

Since the patch of the present invention can prevent a rubber-system macromolecule having a double bond at least in a principal chain thereof from being degraded by adding, to an adhesive base containing the rubber-system macromolecule having a double bond in a principal chain thereof and a nonsteroidal anti-inflammatory analgesic drug, a UVA blocker and/or UVB blocker as a stabilizer for the rubber-system macromolecule, the UVA blocker and/or UVB blocker blocking UV rays effectively, it is possible to suppress a reduction in the adhesive performance.

Furthermore, by adjusting the UVA blocker and/or UVB blocker, a tackifier added, and the amount thereof added, it is possible to control the skin penetrability of the nonsteroidal anti-inflammatory analgesic drug effectively.

BEST MODE FOR CARRYING OUT THE INVENTION

Preferred embodiments of the patch of the present invention are explained in detail below.

The patch of the present invention is characterized in that it contains, in an adhesive base, a nonsteroidal anti-inflammatory analgesic drug, a rubber-system macromolecule having a double bond at least in a principal chain thereof, and a UVA blocker and/or a UVB blocker as a stabilizer for the rubber-system macromolecule having a double bond.

The UVA blocker used in the patch of the present invention may be a dibenzoylmethane derivative, a benzotriazole derivative, etc.

As the dibenzoylmethane derivative, 4-tert-butyl-4'-methoxydibenzoylmethane is preferable, and as the benzotriazole derivative, 2-(2H-benzotriazol-2-yl)-4-methyl-6-[2-methyl-3-[1,3,3,3-tetramethyl-1-[(trimethylsilyl)oxy]disiloxanyl]propyl]phenol and 2-(2-hydroxy-5-methoxyphenyl)-benzotriazole are preferable.

In the patch of the present invention, a particularly preferred UVA blocker is 4-tert-butyl-4'-methoxydibenzoylmethane.

The UVB blocker used in the patch of the present invention is a benzophenone derivative, a cinnamic acid derivative, a camphor derivative, an amino acid-based compound, a benzoylpinacolone derivative, etc.; n-hexyl 2-(4-diethylamino-2-hydroxybenzoyl)benzoate is preferable as the benzophenone derivative, 4-hydroxy-3-methoxycinnamic acid and a branched alkyl ester of 4-hydroxy-3-methoxycinnamic acid such as isostearyl 4-hydroxy-3-methoxycinnamate are preferable as the cinnamic acid derivative and an ester thereof, terephthalylidene-3,3'-dicamphor-10,10'-disulfonic acid is preferable as the camphor derivative, 2-hexyl dimethoxybenzylidenedioxoimidazolidinepropionate is preferable as the amino acid-based compound, and 1-(3,4-dimethoxyphenyl)-4,4-dimethyl-1,3-pentanedione is preferable as the benzoylpinacolone derivative.

The amount of the UVA blocker and/or UVB blocker added to the patch of the present invention is not particularly limited, but it is preferably 0.5 to 20 mass % relative to the entire amount of the preparation, more preferably 1 to 15 mass %, and yet more preferably 2 to 10 mass %. By making the amount of the UVA blocker and/or UVB blocker added be in the above-mentioned range, it is possible to prevent effectively degradation of the rubber-system macromolecule having a double bond in a principal chain thereof while maintaining the performance of the preparation. When the amount of UVA blocker and/or UVB blocker added is more than the above-mentioned range, although the degradation prevention effect is unchanged, since there is a possibility that they might interact with the nonsteroidal anti-inflammatory analgesic drug, thus inhibiting the skin penetrability of the nonsteroidal anti-inflammatory analgesic drug, it is particularly preferable for the amount to be in the above-mentioned range.

The patch of the present invention may further contain an inorganic compound such as zinc oxide, titanium dioxide, talc, kaolin, alumina, or calcium carbonate. When the inorganic compound is added as fine particles of 0.1 μm or less, it may be used as the UVB blocker, and titanium dioxide is preferable.

The patch of the present invention may further contain dibutylhydroxytoluene as an antioxidant. By adding dibutylhydroxytoluene, it is possible to improve the stickiness, etc. of the adhesive base.

The nonsteroidal anti-inflammatory analgesic drug that can be used in the patch of the present invention is not particularly limited as long as it decomposes upon exposure to UV rays to thus form a radical. Examples thereof include ketoprofen, tiaprofenic acid, suprofen, tolmetin, carprofen, benoxaprofen, piroxicam, meloxicam, benzydamine, naproxen, felbinac, diclofenac, ibuprofen, diflunisal, azapropazone, etodolac, valdecoxib, celecoxib, and rofecoxib, and/or pharmaceutically acceptable salts thereof; among them ketoprofen, tiaprofenic acid, suprofen, and tolmetin, which have a benzophenone-like framework in their structure, are preferable, and ketoprofen, which has a benzophenone framework, is particularly preferable. Such nonsteroidal anti-inflammatory analgesic drugs may be used singly or in a combination of two or more types.

The amount of nonsteroidal anti-inflammatory analgesic drug added to the patch of the present invention is not particularly limited, but it is 0.1 to 10 mass % relative to the entire amount of the preparation, and preferably 0.5 to 5 mass %. Setting the amount of nonsteroidal anti-inflammatory analgesic drug added in the above-mentioned range enables an anti-inflammatory analgesic effect to be fully exhibited while achieving preparation stability.

A base used in the patch of the present invention is a rubber-system macromolecule having a double bond at least in a principal chain thereof, and examples thereof include a styrene-isoprene-styrene block copolymer, a styrene-butadiene-styrene block copolymer, a styrene-butadiene copolymer, polyisoprene, and polybutadiene. Among them, the styrene-isoprene-styrene block copolymer is preferable.

As long as it is a rubber-system macromolecule having a double bond at least in a principal chain thereof, it may be a macromolecule having a side chain.

When the styrene-isoprene-styrene block copolymer is used, the mass-average molecular weight is preferably 100,000 to 300,000, and examples thereof include Kraton D-KX401CS and D-1107CU (manufactured by Shell Chemical Corporation), SIS-5000 and SIS-5002 (manufactured by Japan Synthetic Rubber Co., Ltd.), Quintac 3530, 3421, and 3570C (manufactured by Nippon Zeon Corporation), and Solprene 428 (manufactured by Phillips Petroleum Corporation). The base may contain one or more of these styrene-isoprene-styrene block copolymers, and taking into consideration the cohesive strength and ease of handling the amount of copolymer added is preferably 8 to 50 mass % relative to the total amount of the base, more preferably 10 to 40 mass %, and yet more preferably 13 to 30 mass %.

The base of the patch of the present invention has its adhesion to skin, pain when peeled off, reaction with skin, etc. greatly improved by containing a styrene-isoprene-styrene block copolymer having the above-mentioned weight-average molecular weight in the above-mentioned proportion, and preferably by further adjusting the viscosity and the adhesive strength.

Furthermore, as the base of the patch of the present invention, in addition to the rubber-system macromolecule having a double bond in a principal chain thereof, a synthetic rubber or a natural rubber such as a polyisoprene rubber, a polyisobutylene rubber, a natural rubber, a styrene-isoprene copolymer, a styrene-isoprene-butadiene block copolymer, a styrene-ethylene-propylene-styrene block copolymer, etc. may be added.

A preferred adhesive base according to the present invention is one containing a rubber-system macromolecule having a double bond in a principal chain thereof such as a styrene-isoprene-styrene block copolymer, another rubber-system macromolecule such as polyisobutylene, a tackifier, and a plasticizer, and can be prepared by mixing the styrene-isoprene-styrene block copolymer, polyisobutylene and the tackifier at a desired ratio and adjusting, with the plasticizer, the viscosity of the mixture so as to be at the above-mentioned viscosity. The adhesive strength of the patch of the present invention can be adjusted by adjusting mainly the composition of the adhesive base.

The tackifier preferably has a softening point of 60° C. to 150° C.; a rosin ester, a hydrogenated rosin ester, a maleic acid-modified rosin ester, a terpene resin, and a petroleum resin may be used, a hydrogenated rosin ester, a terpene resin, and a petroleum resin are particularly preferable, and a combination of a hydrogenated rosin ester and a terpene resin is most preferable. Specific examples thereof include Ester Gum A, AA-G, H, and HP (manufactured by Arakawa Chemical Industry Co., Ltd.), Hariester L, S, and P (manufactured by Harima Chemicals Co., Ltd.), Pine Crystal KE-100 and KE-311 (manufactured by Arakawa Chemical Industry Co., Ltd.), Hercolyn D (manufactured by Rika Hercules Inc.), Foral 85 and 105 (manufactured by Rika Hercules Inc.), Stebelite Ester 7 and 10 (manufactured by Rika Hercules Inc.), Pentalyn 4820 and 4740 (manufactured by Rika Hercules Inc.), Arkon P-85 and P-100 (manufactured by Arakawa Chemical Industry Co., Ltd.), Escorez 5300 (manufactured by Exxon Chemical Japan Ltd.), and Clearon K, M, P, YS resin, PX1000, PX1150 and PX1200 (manufactured by Yasuhara Chemical Co., Ltd.), and they may be used singly or in a combination of two or more types.

The amount of tackifier added is preferably 3 to 50 mass % relative to the total amount of the base, more preferably 5 to 45 mass %, and yet more preferably 7 to 40 mass %, and the viscosity and the adhesive strength of the base are adjusted so as to be in the above-mentioned ranges. By attaining this proportion, the base thus obtained is greatly improved in terms of adhesive strength, adhesion to the skin, pain when peeled off, skin reaction, etc. It has been found that the above-mentioned tackifier affects the skin penetrability of the nonsteroidal anti-inflammatory analgesic drug due to interaction with the nonsteroidal highly anti-inflammatory analgesic drug and the UVA blocker and/or UVB blocker used in combination. Therefore, in order to prevent crystals of the UVA blocker and/or UVB blocker from precipitating in the adhesive base and prevent the adhesion from being degraded, and maintain a high skin penetrability for the nonsteroidal anti-inflammatory analgesic drug, the amount of tackifier added is particularly preferable 10 to 20 mass %.

The plasticizer preferably has a solution viscosity of 10-100 cSt (40° C.); examples thereof include almond oil, olive oil, camellia oil, persic oil, peanut oil, an olefin acid, and liquid paraffin, and they may be added to the adhesive base singly or as a combination of two or more types. The proportion thereof added is preferably 5 to 70 mass %, more preferably 10 to 60 mass %, and yet more preferably 15 to 55 mass %, relative to the total amount of the base; it is adjusted so that the viscosity and the adhesive strength of the base are within the above-mentioned range. In accordance with this proportion, the base thus obtained is greatly improved in terms of adhesive strength, adhesion to skin, uniform dispersability of the drug in the base, pain when peeled off, damage to the corneum, skin reaction, thermal stability, etc.

The adhesive base of the patch of the present invention may contain a conventionally known filler, antioxidant, solubilizing agent, etc. Examples of fillers that can be used include zinc oxide, aluminum oxide, titanium dioxide, calcium carbonate, synthetic aluminum silicate, silica, magnesium oxide, and a stearic acid metal salt. Examples of antioxidants that can be used include ascorbic acid, tocopherol acetate, natural vitamin E, dibutylhydroxytoluene, and propyl gallate. Examples of solubilizing agents that can be used include oleic acid, benzyl alcohol, isopropyl myristate, crotamiton, oleyl alcohol, eucalyptus oil, limonene, isopulegol, diisopropyl adipate, diethyl sebacate, and other refined oils. Furthermore, a surfactant, a fat, a higher fatty acid, a fragrance, etc. may be contained as necessary. Moreover, skin stimulants (counterirritants) such as L-menthol, camphor, peppermint oil, red pepper extract, capsaicin, benzyl nicotinate, methyl salicylate, and glycol salicylate may be added appropriately as necessary.

With regard to the patch of the present invention, as long as the adhesive base is formed from the above-mentioned composition and the patch has a support for supporting the adhesive base, other layers and components forming same are not particularly limited, and the patch may comprise any layer. For example, the patch of the present invention may contain, in addition to the support and the adhesive layer, a release liner layer provided on the adhesive layer, etc.

The support may be formed from, for example, woven cloth, non-woven cloth, polyurethane, polyester, polyvinyl acetate, polyvinylidene chloride, polyethylene, polyethylene terephthalate, polybutylene terephthalate, paper, aluminum sheet, or a composite material thereof.

Furthermore, the support of the present invention may be a conventionally disclosed support onto which a UV blocker is adsorbed, etc.

A process for producing the patch of the present invention is now explained. As one example, the viscosity and the adhesive strength are first adjusted by adding a tackifier and a plasticizer to a styrene-isoprene-styrene block copolymer and polyisobutylene, and a filler, an antioxidant, etc. are optionally added at a predetermined ratio to give a mixture, and this is stirred under an atmosphere of nitrogen gas while heating to give a solution. The stirring temperature is 100° C. to 200° C. and the stirring time is 30 to 120 minutes. Subsequently, a medically effective component is added at a temperature range from 100° C. to 200° C. while stirring the solution, and mixing is further carried out for 1 to 30 minutes to give a uniform solution. Subsequently, this solution may be directly spread over a support by a standard method and covered with a peel-off cover, or first spread on a peel-off cover and then transferred to a support by compression. The peel-off cover may be selected appropriately from a peel-off paper, cellophane, or film such as polyethylene, polypropylene, or polyester that has been subjected to a peel-off treatment.

EXAMPLES

Production of Preparation 17 parts by mass of a styrene-isoprene-styrene block copolymer (SIS5200P: manufactured by JSR Corporation), 10 parts by mass of polyisobutylene (L-100: manufactured by Exxon Mobil), 13 parts by mass of a petroleum resin (Arkon P-70: manufactured by Arakawa Chemical Industry Co., Ltd.), 44 parts by mass of liquid paraffin (Christol J-352: manufactured by Esso Petroleum Ltd.), and 2 parts by mass of synthetic aluminum silicate were stirred under an atmosphere of nitrogen gas while heating to give a solution (Step A). The stirring temperature was 100° C. to 200° C., and the stirring time was 30 to 120 minutes. Subsequently, 3 parts by mass of crotamiton, 6 parts by mass of 4-tert-butyl-4'-methoxydibenzoylmethane (hereinafter, abbreviated to BM-DBM), 2 parts by mass of ketoprofen, and 3 parts by mass of 1-menthol were added to the above-mentioned solution when the stirring temperature therefor was in the range of 100° C. to 200° C., and mixed for 5 to 30 minutes to give a uniform solution, which was a base for a plaster preparation (Step B). This base was spread over a silicone-treated polyester film at a mass of 1 g per 70 $cm^2$, covered with a polyester non-woven cloth, transferred by compression, and cut to a desired size to give a tape preparation of the present invention (Preparation 1). Preparations 2 to 11 were obtained in the same manner as above using formulations described in Table 1.

TABLE 1

| | Prep. 1 | Prep. 2 | Prep. 3 | Prep. 4 | Prep. 5 | Prep. 6 | Prep. 7 | Prep. 8 | Prep. 9 | Prep. 10 | Prep. 11 | Comp. Ex. |
|---|---|---|---|---|---|---|---|---|---|---|---|---|
| SIS block copolymer | 17 | 17 | 17 | 18 | 18 | 18 | 18 | 18 | 18 | 18 | 17 | 18 |
| Polyisobutylene | 10 | 10 | 10 | 10 | 10 | 11 | 10 | 10 | 10 | 10 | 10 | 11 |
| Liquid paraffin | 44 | 42 | 44 | 46 | 48 | 50 | 48 | 48 | 48 | 45 | 42 | 47 |
| Petroleum resin | 13 | — | — | — | — | — | 3 | 5 | — | — | — | 14 |
| Hydrogenated rosin ester | — | 15 | 13 | 13 | 11 | 8 | 8 | 6 | 6 | 8 | 8 | — |
| Terpene resin | — | — | — | — | — | — | — | — | 5 | 6 | 10 | — |
| Synthetic aluminum silicate | 2 | 2 | 2 | — | — | — | — | — | — | — | — | 2 |
| Zinc stearate | — | — | — | 2 | 2 | 2 | 2 | 2 | 2 | 2 | 2 | — |
| Crotamiton | 3 | 3 | 3 | 3 | 3 | 3 | 3 | 3 | 3 | 3 | 3 | — |
| BM-DAM | 6 | 6 | 6 | 3 | 3 | 3 | 3 | 3 | 3 | 3 | 3 | 3 |
| L-Menthol | 3 | 3 | 3 | 3 | 3 | 3 | 3 | 3 | 3 | 3 | 3 | 3 |
| Ketoprofen | 2 | 2 | 2 | 2 | 2 | 2 | 2 | 2 | 2 | 2 | 2 | 2 |
| Total (wt. %) | 100 | 100 | 100 | 100 | 100 | 100 | 100 | 100 | 100 | 100 | 100 | 100 |
| Amount of KP transferred - Man[mg/9 cm2] | — | 0.97 | 0.93 | 1.15 | 1.30 | — | — | — | — | — | — | — |
| Amount of KP transferred - Hr [mg/1.77 cm2] | — | — | — | — | About 120 | 153.60 | — | — | 168.7 | 150.5 | 123.8 | — |
| Amount of BM-DAM transferred [μg/3.14 cm2] | — | — | — | 16.42 | 19.63 | — | — | — | — | — | — | — |
| Amount of BM-DAM transferred [μg/1.77 cm2] | — | — | — | — | About 7 | 10.64 | — | — | 8.49 | 9 | 7.98 | — |
| BM-DAM crystals observed | C | B | B | A | A | C | C | C | A | A | A | — |
| Skin adhesion | B | B | B | A | A | A | A | A | A | A | A | — |

Hr: Abbreviation for hairless mouse

Example 1

Preparation 1 and a comparative example formed by excluding 4-tert-butyl-4'-methoxydibenzoylmethane (BM-DBM) from the formulation of Preparation 1 were subjected to a drug light stability test and an adhesive base degradation test as follows.

(1) Light Stability Test

Each preparation was left to stand in a place where it was fully exposed to direct sunlight with a liner side facing up, and the percentage drug remaining in the base after 4 hours was measured by liquid chromatography. The results are given in Table 2.

(2) Adhesive Base Degradation Test

Each preparation was left to stand in a place where it was fully exposed to direct sunlight with a liner side facing up, and the cohesive strength (stickiness) of the base after 4 hours was examined. The results are given in Table 2.

TABLE 2

| | Amount of ketoprofen remaining | State of adhesive base |
|---|---|---|
| Without UVA blocker | 53.0% | Sticky Stringy |
| With UVA blocker | 99.7% | No stickiness No stringiness |

Since the decomposition of ketoprofen can be suppressed by the addition of a UVA blocker and/or UVB blocker, decomposition of the styrene-isoprene-styrene block copolymer due to radical formation can be suppressed, and stickiness, etc. of the adhesive base can be prevented.

Example 2

Ketoprofen Skin Transfer Test (Man)

2% ketoprofen (KP) preparations of 3 cm×3 cm (Preparations 2 to 5) produced in accordance with the formulations in Table 1 were affixed to the back of six healthy male adults. The preparations were peeled off after 6 hours, and the ketoprofen remaining in the preparations was extracted and then quantitatively measured by HPLC. The amount of ketoprofen transferred to the skin was calculated by subtracting the amount remaining from the initial ketoprofen content in the preparations.

In the preparations containing 6% BM-DBM (Preparations 2 and 3), the amount of hydrogenated rosin ester (KE-311E) added had little effect on the amount of ketoprofen transferred to the skin. On the other hand, in the preparations containing 3% BM-DBM (Preparations 4 and 5), the smaller the amount of hydrogenated rosin ester added, the larger the amount of ketoprofen transferred to the skin. When the amount of hydrogenated rosin ester added was the same, the preparation containing 3% BM-DBM exhibited a larger amount of ketoprofen transfer to the skin than did the preparation containing 6% BM-DBM.

It is surmised that, among the tackifying resins, the hydrogenated rosin ester has excellent characteristics in terms of dissolving ketoprofen.

Example 3

Drug Skin Transfer Test (Hairless Mouse)

2% ketoprofen (KP) preparations of 3 cm×3 cm produced in accordance with the formulations in Table 1 were affixed to skin removed from hairless mice, and stored for 6 hours while being maintained at 32° C. The preparations were subsequently peeled off from the skin, the skin was homogenized, ketoprofen and BM-DBM were then extracted and quantitatively measured, and the amounts thereof per preparation transferred to the skin were calculated.

In the preparations containing 3% BM-DBM, a preparation having a smaller amount of hydrogenated rosin ester (KE-311E) added showed a larger amount of ketoprofen and BM-DBM transfer to the skin. It is surmised that since the hydrogenated rosin ester functions as a solubilizing agent for BM-DBM in the same manner as for ketoprofen, the distribution ratio to the skin increases.

Example 4

Preparation Stability Test

2% ketoprofen (KP) preparations of 10 cm×7 cm produced in accordance with the formulations in Table 1 were visually examined at the time of production, and one month and three months thereafter, and an evaluation was made in terms of BM-DBM crystal precipitation, etc. The results are given in Table 1.

A: no crystal precipitation after 3 months, B: no crystal precipitation after 1 month, C: no crystal precipitation when produced, D: crystal precipitation when produced Example 5

Preparation Affixation Test (Man)

2% ketoprofen (KP) preparations of 10 cm×7 cm produced in accordance with the formulations in Table 1 were affixed to the knee of 30 subjects, and adhesion after 6 hours (an overall evaluation of state of affixation, residual plaster after the preparation was peeled off, stickiness and itchiness after the preparation was peeled off) was evaluated based on predetermined evaluation criteria. The results are given in Table 1.

A: very good, B: good, C: usable, D: poor

Preparations 4 to 11 showed overall good adhesion. Preparations 1 to 3 showed slightly poorer adhesion compared with Preparations 4 to 11.

The invention claimed is:

1. A patch preparation comprising a support and an adhesive base, the adhesive base containing 8 to 50 mass % relative to the total amount of the adhesive base of a rubber-system macromolecule having a double bond at least in a principal chain thereof, wherein the rubber system macromolecule having a double bond at least in a principal chain thereof is selected from the group consisting of a styrene-isoprene-styrene block copolymer, a styrene-butadiene-styrene block copolymer, a styrene-butadiene copolymer, polyisoprene, and polybutadiene; 0.1 to 10 mass % relative to the entire amount of the preparation of ketoprofen or a pharmaceutically acceptable salt thereof as a nonsteroidal anti-inflammatory analgesic drug; 10 to 20 mass % relative to the total amount of the adhesive base of a tackifier comprising a combination of hydrogenated rosin ester and a terpene resin; and 2-10 mass % relative to the total amount of the adhesive base of 4-tert-butyl-4'-methoxydibenzoylmethane as a stabilizer for the rubber-system macromolecule.

2. The patch preparation according to claim 1, wherein it contains zinc oxide or titanium dioxide.

3. The patch preparation of claim 1, wherein said preparation is a plaster.

4. The patch preparation of claim 1, wherein it contains 0.5 to 5 mass % relative to the entire amount of the preparation of ketoprofen or pharmaceutically acceptable salts thereof as a nonsteroidal anti-inflammatory analgesic drug.

5. The patch preparation of claim 1, wherein the total amount of hydrogenated rosin ester and a terpene resin is 11 to 14 mass % relative to the amount of the adhesive base, and the amount of hydrogenated rosin ester is 6 to 8 mass % relative to the total amount of the adhesive base.

6. The patch preparation of claim 4, wherein the total amount of hydrogenated rosin ester and a terpene resin is 11 to 14 mass % relative to the amount of the adhesive base, and the amount of hydrogenated rosin ester is 6 to 8 mass % relative to the total amount of the adhesive base.

* * * * *